United States Patent [19]

Mochida

[11] 4,379,136
[45] Apr. 5, 1983

[54] SOLID STICK OF POWDER FOR COSMETIC AND TOILET USE AND A METHOD FOR PREPARING THEREOF

[76] Inventor: Nobuo Mochida, 4-17-2, Minamiogikubo, Suginami-ku, Tokyo, Japan

[21] Appl. No.: 967,085

[22] Filed: Dec. 6, 1978

[30] Foreign Application Priority Data

Dec. 7, 1977 [JP] Japan ................................ 52-146169

[51] Int. Cl.$^3$ ...................... A61K 7/32; A61K 31/745
[52] U.S. Cl. ................................ 424/65; 424/DIG. 5; 424/63; 424/83; 424/357
[58] Field of Search ...................... 424/DIG. 5, 65, 83

[56] References Cited

U.S. PATENT DOCUMENTS

| 2,623,003 | 12/1952 | Friedlob et al. | 424/DIG. 5 |
| 2,838,442 | 6/1958 | McMaster | 424/DIG. 5 |
| 2,865,806 | 12/1958 | Bulloff | 424/DIG. 5 |
| 3,196,079 | 7/1965 | Blaustein | 424/83 |
| 3,211,619 | 10/1965 | Buchwalter | 424/DIG. 5 |
| 3,255,082 | 6/1966 | Barton | 424/DIG. 5 |
| 3,576,776 | 4/1971 | Muszik et al. | 424/DIG. 5 |
| 3,800,034 | 3/1974 | Kircher et al. | 424/DIG. 5 |

FOREIGN PATENT DOCUMENTS 1230884  5/1971  United Kingdom ......... 424/DIG. 5

Primary Examiner—Dale R. Ore
Attorney, Agent, or Firm—Armstrong, Nikaido, Marmelstein & Kubovcik

[57] ABSTRACT

A solid stick of powder for cosmetic and toilet use prepared by compressing at an impact pressure of about 4.0 to 8.0 kg/cm$^2$ a pulverulent blend of raw materials of powders and binding aids. Said stick can be applied to skin directly and has excellent properties of adhesion and feel.

3 Claims, No Drawings

SOLID STICK OF POWDER FOR COSMETIC AND TOILET USE AND A METHOD FOR PREPARING THEREOF

BACKGROUND OF THE INVENTION

1. Field of the Invention

This invention relates to a special powder preparation for cosmetic and toilet use compressed into a solid stick and to a method for preparing the same. In particular, this invention relates to a solid stick of powder containing talc and other raw materials of cosmetic and toilet powder as principal ingredients, binding aids such as particulate polyethylene, and several other ingredients, and also to a method of preparing same.

A solid stick of powder according to this invention is prepared by mixing with agitation the above mentioned components together and then compressing by impact a definite quantity of the mixture to form a solid stick of powder, which can be applied directly to skin, and has adequate strength, is adhesive to skin, and has a smooth feeling.

2. Statement of the Prior Art

In conventional powders for cosmetic and toilet use, there are various compositions such as face paints, face cakes, talcum powders, baby powders, antisudorific agents and the like. However, they are in particulate form, flat solid form, aerosol form or the like. Heretofore, there has not been disclosed a powder for cosmetic and toilet use which is compressed into a solid stick form using particulate materials only.

Lipsticks, hair cosmetics and other cosmetics contain powder materials, but they are molded into a solid stick form in a fluidized condition. The present invention is the first instance in which a solid stick of powder for cosmetic and toilet use is compressed by impacting the particulate materials.

In conventional techniques it has not been possible to produce a product having a suitable product strength without adversely effecting the feel a user derives from the product when those techniques are used to produce a product in which only particulate materials are shaped into a solid stick.

Prior art cosmetic and toilet powders possess the following disadvantages: (1) in a particulate or aerosol form, the dust created is drawn through the respiratory system resulting in undesirable effects on the human body, and in a particulate form product, it is bulky with respect to its weight and is troublesome in handlings; (2) in the case of an aerosol, a chilling effect will accompany the application; and with a flat solid product, it cannot be directly applied and necessitates making use of a powder puff for application and such application is not sanitary due to its tendency of contamination with dust or various germs.

BRIEF SUMMARY OF THE INVENTION

In accordance with this invention, there is provided a solid stick of powder for cosmetic and toilet use such as a baby powder or the like, which affords an improved application feeling and which is economical, sanitary and practical, and which does not have the defects of conventional powders such as dustability, a bulky vessel, contamination with miscellaneous substances and various germs, and excessive waste. The powder product according to this invention, can be safely, cleanly and conveniently applied directly to the skin.

Usually, the raw materials of powders for cosmetic and toilet use typically include talc, kaolin, calcium carbonate, magnesium carbonate, starch, zinc white, titanium dioxide, metallic soaps, silica, particulate resins, hydrocarbons, fats and oils, waxes, fatty acids, lower and higher alcohols, esters, phospholipids; and surface active agents, pigments, preservatives and the like. These have some bonding ability.

In addition to one or more materials selected from the group consisting of the above raw materials of powders for cosmetic and toilet use, a solid stick of powder produced according to the present invention includes one or more so-called binding aids selected from the group consisting of agents such as magnesium silicoaluminate light fine ground powder, aerosil, lipophilic aerosil, alcohols, propylene glycol, squalane, mineral oils, lanoline, cholesterol, oleic amide, zinc stearate, nylon, polyethylene, corn starch, silicone oil, methylcellulose, CMC, kaolin, bentonite and the like. Preferably, as shown in the following examples, the solid stick will comprise one or more components consisting of polyethylene, zinc stearate, starch such as corn starch, silicone oil, lanolin and kaolin. Particularly, polyethylene is an essential ingredient as a binding aid.

DETAILED DESCRIPTION OF THE PREFERRED EMBODIMENTS

Specific examples will hereinafter be described, wherein all percentages are by weight.

EXAMPLE 1

Raw materials taken at the proportion of 75% talc, 3% zinc oxide, 14% starch, and 8% particulate polyethylene, and an adequate amount of perfume are placed into a fluidizable high speed agitation powder mixer, and then mixed at about 90° C. until the raw materials are well mixed together.

After the components are well mixed, the temperature is raised to about 110° C. and the mixing is continued with agitation for an additional 30 to 60 minutes. At the end of the agitation mixing, the resultant mixture is allowed to cool spontaneously, and the granulated particles of the mixture are ground in a hammer-mill at a temperature below 80° C. to fine particles. A 55 g portion of the resultant particles is placed into a cylindrical impact molding machine, in which it is compressed at an impact pressure of about 5 kg/cm$^2$ to form a solid stick of powder of about 30 mm in diameter and 40 mm to 50 mm in length. The product obtained above is referred to as Product A.

EXAMPLE 2

Raw materials having the proportion of 80% talc, 3% kaolin, 3% zinc stearate, 10% corn starch and 4% particulate polyethylene, and an adequate amount of perfume are placed into a fluidizable high speed agitation powder mixer, and then mixed at about 90° C. to obtain a well mixed blend of raw materials. After the materials are well mixed, the temperature is raised to about 120° C. and agitation mixing is continued for about 50 minutes.

After mixing, the resultant mixture is allowed to cool spontaneously and the resultant granulated particles of the mixture are finely ground in a hammer-mill at a temperature below 80° C. A 55 g portion of the ground particles is taken and placed into a cylindrical impact molding machine, and is compressed at an impact pressure of about 5 kg/cm$^2$ to form a solid stick of powder of about 30 mm in diameter and about 40 mm to 50 mm in length.

EXAMPLE 3

Following the procedure described in Example 2 except that the raw materials have the proportions of 58% talc, 5% zinc oxide, 2% zinc stearate, 20% corn starch, 3% silicon and 12% particulate polyethylene, a solid stick of powder is formed.

EXAMPLE 4

Following the procedure described in Example 2 except that the raw materials have the proportions of 64% talc, 25% corn starch, 5% lanolin and 6% particulate polyethylene, a solid stick of powder is formed.

EXAMPLE 5

Following the procedure described in Example 1 except that an impact pressure of 4.5 kg/cm² is applied, a solid stick of powder is formed. This product is referred to as Product B.

EXAMPLE 6

Following the procedure described in Example 1 except that an impact pressure of 5.5 kg/cm² is applied, a solid stick of powder is formed. This product is referred to as Product C.

EXAMPLE 7

Following the procedure described in Example 1 except that the agitation mixing is carried out at 105° C., a solid stick of powder is formed. This product is referred to as Product D.

EXAMPLE 8

Following the procedure described in Example 1, but using the corn starch in an amount of 10% and the particulate polyethylene in an amount of 12%, a solid stick of powder is formed. This product is referred to as Product E.

Of the above examples, Products, A, B, C, D and E are conveniently taken and the following tests are conducted on them.

(I) Strength (Compressive breaking data)
Instrument employed:
Shimazu universal tester (Type IM-100)
(Condition: 4 mm/min)

| Product | Strength (kgf) (Vertical direction) | | | | Strength (kgf) (Horizontal direction) | | | |
|---|---|---|---|---|---|---|---|---|
| | 1 | 2 | 3 | Mean | 1 | 2 | 3 | Mean |
| A | 29.2 | 25.0 | 28.5 | 27.6 | 23.0 | 23.0 | 26.9 | 24.3 |
| B | 16.5 | 15.9 | 16.4 | 16.3 | 10.2 | 8.9 | 9.5 | 9.5 |
| C | 38.5 | 33.9 | 37.0 | 36.5 | 26.8 | 29.0 | 30.2 | 28.7 |
| D | 19.6 | 20.6 | 22.0 | 20.7 | 17.8 | 17.7 | 18.0 | 17.8 |
| E | 45.4 | 48.3 | 46.9 | 46.9 | 32.3 | 40.5 | 35.1 | 36.0 |

A product having the following strengthes is considered to be satisfactory for transportation and application for cosmetic and toilet use:
(1) greater than 10.0 kgf in vertical direction,
(2) greater than 6.0 kgf in horizontal direction.

Since the product strength is inversely proportional to the adhesive property to the skin as described below, the following ranges of strength are considered to be adequate with respect to strength and adhesive property:

(1) 28.0±18.0 kgf in vertical direction,
(2) 24.0±18.0 kgf in horizontal direction.

(II) Adhesion to skin

A coated amount (in grams) on a 500 cm² side of a polyethylene foam board of 1 mm thickness, applied by hand with a light touch. (These values are proportional to adherence to skin).

| Sample | Test | | | | | |
|---|---|---|---|---|---|---|
| | 1st | 2nd | 3rd | 4th | 5th | Mean |
| Product A | 0.75 | 0.78 | 0.78 | 0.72 | 0.74 | 0.754g |
| Product B | 1.01 | 0.97 | 0.98 | 1.00 | 0.98 | 0.988g |
| Product C | 0.49 | 0.50 | 0.46 | 0.53 | 0.48 | 0.492g |
| Product D | 0.77 | 0.75 | 0.70 | 0.81 | 0.75 | 0.756g |
| Product E | 0.38 | 0.40 | 0.41 | 0.41 | 0.38 | 0.396g |
| Flat solid powder produced by W Co. | 0.30 | 0.32 | 0.25 | 0.26 | 0.29 | 0.284g |
| Pulverized powder produced by W Co. | 0.78 | 0.80 | 0.81 | 0.79 | 0.80 | 0.796g |

From the above data, it can be seen that the adhesive properties of the products according to this invention are higher than the existing flat solid powder product. Those products according to the invention having a higher adhesive property show an equivalent or much higher adhesion than the pulverized powder product, and, therefore, can be applied with fully satisfactory results.

(III) Practical comparison

| Type | Sample | Dustability | Touch | Strength |
|---|---|---|---|---|
| Solid and stick-like form | Product A | — | excellent | high |
| | Product B | + | excellent | medium |
| | Product C | — | good | high |
| | Product D | — | excellent | high |
| | Product E | — | good | high |
| Solid and flat form | Product (W Co.) | + | good | low |
| | Product (X Co.) | ++ | useful | medium |
| | Product (Y Co.) | ++ | good | low |
| Particulated | Product (W Co.) | +++ | excellent | |
| | Product (Y Co.) | +++ | excellent | |
| Aerosol | Product (Z Co.) | +++ | not good | |

Evaluation standards
(A) Dustability:

| Rate of dusting | 0–5% | — |
|---|---|---|
| | 5–10% | + |
| | 10–20% | ++ |
| | 20% or more | +++ |

Evaluation procedure:

A vertical polyethylene foam board was used in the usual manner, and calculations made according to the following equation:

$$\frac{\text{(reduced weight)} - \text{(residual weight)}}{\text{(reduced weight)}} \times 100 \ (\%)$$

wherein reduced weight refers to the reduced weight of the sample after application by hand with light tough to a polyethylene foam board, and residual weight refers to the weight adhered to the polyethyelen foam board.
(B) Feeling:

| excellent | smooth and soft |
|---|---|
| good | smooth but somewhat inferior to excellent |
| useful | conventional |

-continued

| not good | inferior |

(c) Strength: number of times of dropped from 50 cm height until the sample collapsed.

| high | 5 times or more |
| medium | 3 or 4 times |
| low | less than 3 times |

(IV) Degradation on aging (accelerated test)

Condition 1: repetition of the cycle of standing at 45° C. for one day followed by 0° C. for one day.

Condition 2: standing at 45° C. and 90% humidity.

As shown in the following table, in both conditions 1 and 2, there was no change after 60 days. Thus, it was concluded that such conditions had no deleterious effects on product A. (In addition, the values of compressive breaking strength and water content in the following table are within the ranges of error of measurement, and it may be said that material change did not occur.)

As can be seen from the results of the following tests, the instant product is an excellent product as a solid stick of powder for cosmetic and toilet use.

Sample: Product A (Example 1)
(10 samples per item)

| | | Evaluation Item | | | | Compressive breaking strength | | Moisture |
| Condition | | Appearance | Color | Odor | Touch | (vert.) | (horiz.) | Content |
| --- | --- | --- | --- | --- | --- | --- | --- | --- |
| I | Before test | — | white | — | excellent | mean 26.0 | mean 24.2 | mean 0.03% |
| | After 60 days | unchanged | unchanged | unchanged | excellent | mean 26.2 | mean 24.2 | mean 0.03% |
| II | Before test | — | white | — | excellent | mean 27.2 | mean 24.5 | mean 0.03% |
| | After 60 days | unchanged | unchanged | unchanged | excellent | mean 26.9 | mean 24.1 | mean 0.04% |

The present invention consists in compressing into a solid stick a powder for cosmetic and toilet use and to a process for preparing the same. Said product may be composed of particulate resins, fat and oils, or natural and synthetic water-soluble high molecular materials as binding aids. Also, pulverized raw materials can be compressed by impacting without a binding aid and then coating them with a component such as a resin or the like to make it possible to retain its strength.

What is claimed is:

1. A method for manufacturing a solid stick of powder for cosmetic and toilet use comprising the steps of, blending (1) one or more particulate materials selected from the group consisting of talc, kaolin, calcium carbonate, magnesium carbonate, starch, zinc white, titanium dioxide, metallic soap, silica; particulate resin, hydrocarbons, fats and oils, waxes, fatty acids, lower and higher alcohols, esters, and phospholipids; (2) one or more ingredients consisting of surface active agents, perfumes, pigments and preservatives and (3) as a binding aid, one or more ingredients selected from the group consisting of particulate polyethylene, zinc stearate, corn starch, silicone oil, lanolin and kaolin, and mixing with agitation at a temperature of from 90° C. to 160° C.; pulverizing the resultant mixture, and compressing said pulverized material at an impact pressure of about 3.0 kg/cm$^2$ to 8.0 kg/cm$^2$ to form a solid stick.

2. A method for manufacturing a solid stick of powder for cosmetic and toilet use according to claim 1, wherein 2% to 15% by weight of particulate polyethylene is formulated as said binding aid.

3. A method for manufacturing a solid stick of powder for cosmetic and toilet use according to claim 2, wherein the impact pressure is about 3.5 kg/cm$^2$ to about 5.5 kg/cm$^2$.

* * * * *